(12) United States Patent
Paikin et al.

(10) Patent No.: US 8,496,982 B2
(45) Date of Patent: Jul. 30, 2013

(54) CALCIUM ENRICHMENT COMPOSITIONS METHOD OF PRODUCTION THEREOF AND USE

(75) Inventors: Michael Paikin, Yoqneam (IL); Nissim Guigui, Misgav (IL)

(73) Assignee: Gadot Biochemical Industries Ltd, Haifa Bay (IL)

( * ) Notice: Subject to any disclaimer, the term of this patent is extended or adjusted under 35 U.S.C. 154(b) by 556 days.

(21) Appl. No.: 12/225,379

(22) PCT Filed: Mar. 22, 2007

(86) PCT No.: PCT/IL2007/000375
§ 371 (c)(1),
(2), (4) Date: Jan. 5, 2009

(87) PCT Pub. No.: WO2007/107999
PCT Pub. Date: Sep. 27, 2007

(65) Prior Publication Data
US 2009/0142451 A1    Jun. 4, 2009

(30) Foreign Application Priority Data

Mar. 22, 2006   (IL) .......................................... 174477

(51) Int. Cl.
A23K 1/175   (2006.01)
A23L 1/30    (2006.01)
A23L 2/38    (2006.01)
A23B 7/157   (2006.01)
A23B 7/154   (2006.01)

(52) U.S. Cl.
USPC ............ 426/74; 426/267; 426/321; 426/590; 426/648

(58) Field of Classification Search
USPC .............................................. 426/74, 267, 648
See application file for complete search history.

(56) References Cited

U.S. PATENT DOCUMENTS

| 4,214,996 A |   | 7/1980  | Buddemeyer et al. |
| 4,351,735 A |   | 9/1982  | Buddemeyer et al. |
| 4,551,342 A |   | 11/1985 | Nakel et al. |
| 4,737,375 A |   | 4/1988  | Nakel et al. |
| 4,772,467 A |   | 9/1988  | Pak |
| 4,786,518 A |   | 11/1988 | Nakel et al. |
| 4,851,221 A | * | 7/1989  | Pak et al. ............. 424/693 |
| 4,895,980 A |   | 1/1990  | Walsdorf et al. |
| 4,985,593 A |   | 1/1991  | Walsdorf et al. |
| 4,992,282 A |   | 2/1991  | Mehansho et al. |
| 5,149,552 A | * | 9/1992  | Vidal et al. ............. 426/321 |
| 5,204,134 A |   | 4/1993  | Girsh |
| 5,213,134 A |   | 5/1993  | Orlandi |
| 5,213,838 A |   | 5/1993  | Sheikh |
| 5,219,889 A |   | 6/1993  | Walsdorf et al. |

(Continued)

FOREIGN PATENT DOCUMENTS

| GB | 597936      | 2/1948 |
| GB | 2 299 992 A | 10/1996 |
| JP | 8-33462 A   | 2/1986 |

(Continued)

*Primary Examiner* — Rena Dye
*Assistant Examiner* — Assaf Zilbering
(74) *Attorney, Agent, or Firm* — Vorys, Sater, Seymour and Pease; Susanne M. Hopkins

(57) ABSTRACT

The present invention concerns a stable calcium composition, a process for its preparation and its use for enriching food and beverages. The calcium composition comprises a calcium source, a citrate and a metal source selected from alkali and/or alkaline source.

21 Claims, 2 Drawing Sheets

U.S. PATENT DOCUMENTS

| | | | |
|---|---|---|---|
| 5,260,082 A * | 11/1993 | delValle et al. | 426/549 |
| 5,445,837 A | 8/1995 | Burkes et al. | |
| 5,486,506 A | 1/1996 | Dunn | |
| 5,662,954 A | 9/1997 | Joiner | |
| 5,928,691 A * | 7/1999 | Reddy et al. | 426/74 |
| 6,036,985 A * | 3/2000 | Jacobson et al. | 426/74 |
| 6,248,376 B1 | 6/2001 | Buddemeyer et al. | |
| 6,261,610 B1 * | 7/2001 | Sher et al. | 426/74 |
| 6,287,607 B2 * | 9/2001 | Pak et al. | 424/682 |
| 6,599,544 B2 | 7/2003 | Buddemeyer et al. | |
| 6,828,130 B2 | 12/2004 | Chatterjee et al. | |
| 6,887,897 B2 | 5/2005 | Walsdorf et al. | |
| 2005/0181096 A1 | 8/2005 | Zeller et al. | |

FOREIGN PATENT DOCUMENTS

| | | |
|---|---|---|
| JP | 8-157380 A | 6/1986 |
| JP | 8-198803 A | 8/1986 |
| JP | 9-252747 A | 9/1997 |
| JP | 2002-65209 A | 3/2002 |
| WO | 88/03762 A1 | 6/1988 |
| WO | 01/05250 A1 | 1/2001 |

* cited by examiner

CALCIUM ENRICHMENT COMPOSITIONS METHOD OF PRODUCTION THEREOF AND USE

FIELD OF THE INVENTION

This invention relates to calcium containing compositions, process for their production and their use. More particularly, this invention is directed to stable calcium-containing compositions for use as food and beverage additives.

BACKGROUND OF THE INVENTION

Mineral and vitamin supplements are often used to fortify the composition of food and beverages, both for human and veterinary use. For example, U.S. Pat. No. 4,772,467 to Pak et al, discloses the use of citrate based calcium sources for increasing the bioavailability of the calcium. U.S. Pat. No. 4,786,518 to Nakel et al., describes nutritional supplements comprising iron-sugar complexes. U.S. Pat. No. 4,992,282 to Mehansho et al. describes stable nutritional vitamin and mineral supplemented beverages.

It is known that the recommended daily allowance (RDA) of calcium, for example, is around 1200 mg per day for an adult. Most of the dietary calcium in a western diet is from cow milk and other dairy products. The calcium content of cow milk is typically in the range of 900-1100 mg per liter, such that one liter almost provides the RDA. Cow milk substitutes such as soy milk or rice milk provide much less calcium than cow milk and almost all the Calcium is added artificially.

Calcium supplements find wide applications as food and beverage supplements. They are used, inter alia, to compensate calcium loss from the human body, as is exhibited in osteoporosis. For example, U.S. Pat. No. 4,994,283 to Mehansho et al. discloses iron-calcium mineral supplements with enhanced bioavailability. U.S. Pat. No. 5,445,837 to Burkes et al., discloses as sweetener supplement fortified with a concentrated bioavalible calcium source and process for making them. U.S. Pat. No. 5,486,506 to Andon discloses a concentrated bioavalible calcium source. U.S. Pat. No. 6,828,130 to Chatterjee et al., discloses methods for production of gluconate salts. U.S. Pat. No. 6,887,897 to Walsdorf, Sr., et al. discloses calcium glutarate supplements and phosphorus binders.

Numerous other relevant patents in the art of food and beverage supplements include: U.S. Pat. Nos. 4,214,996; 4,351,735; 4,551,342; 4,737,375; 4,851,221; 4,895,980; 4,985,593; 5,204,134; 5,213,134; 5,213,838; 5,219,889; 5,928,691; 6,287,607; 6,248,376 and 6,599,544.

Buddemeyer et al., disclose phosphate containing compositions for use as additives to milk in U.S. Pat. No. 6,248,376 and U.S. Pat. No. 6,599,544.

SUMMARY OF THE INVENTION

The present invention is directed to edible calcium comprising compositions that are stable in food and beverages. The calcium comprising compositions are stable in beverages, or in their concentrates, and do not separate out of the liquid phase even under long storage periods. The calcium comprising composition of the present invention is palatable and does not affect the organoleptic properties of the beverage or beverage concentrate to which it is introduced and thus serves as an effective calcium supplement (fortifier) for beverages and solid food.

Thus the present invention is directed to a dry calcium rich composition comprising:
(i) at least one source of calcium;
(ii) at least one source of metal selected from an alkaline metal other than calcium or an alkali metal; and
(iii) at least one source of citrate;
wherein the composition has a bulk density of less than 0.4-0.5 g/cm$^3$, comprises at least 15% (wt/wt) calcium and at least 66% (wt/wt) of citrate on dry weight basis. More preferably the composition comprises 15% to 20% (wt/wt) calcium and at least 71% (wt/wt) citrate on a dry basis.

The composition may further comprise 7-10% crystalline water. It may further comprise stabilizers, coloring agents or emulsifiers.

In particular, the calcium rich composition of the invention is used to enrich beverages with calcium, especially in milk, milk-like beverages and naturally or artificially fortified protein containing beverages. It may be either soluble in the beverage or exist as a suspended addition. The calcium enriched composition introduced into a beverage is stable for a period of at least 10 to 70 days wherein less than 5% (wt/wt) of the composition sediments out of the beverage. It should be noted that "stable" relates to the fact that the calcium enriched composition remains within the liquid phase substantially without sedimenting out. By "substantially without" it is meant that less than 5% of the composition is precipitated. Remaining within the liquid means at least one of remaining suspended, remaining dissolved and remaining bound to a suspended solid or liquid.

The calcium source is selected from the group consisting of calcium hydroxide, calcium oxide, calcium carbonate, calcium propionate, calcium gluconate, calcium citrate, calcium stearate, calcium fumarate, calcium glycerophosphate.

The citrate is selected from the group consisting of citric acid, citric acid monohydrate, citric acid mono-, di- or tri-sodium salt, citric acid mono-, di- or tri-potassium salt or ammonium citrate.

The at least one metal source is selected from the group consisting of a source of sodium, a source of potassium, a source of magnesium or their mixtures. The potassium source is selected from potassium hydroxide, potassium citrate, potassium carbonate, potassium bicarbonate or their mixtures. The magnesium source is selected from magnesium oxide, magnesium hydroxide, magnesium carbonate, magnesium citrate or their mixtures. The sodium source selected from sodium hydroxide, sodium citrate, sodium carbonate, sodium bicarbonate or their mixtures.

Preferably, the calcium enriched dry composition of the present invention comprises a molar ratio of 3-4.5 citrate; 4-6 calcium; and 2-3 of at least one metal source. Such a preferred composition may comprise: (i) a molar ratio of citrate 3-4.5: calcium 4-6: potassium 2-3: and magnesium 0-1; (ii) a molar ratio of citrate 4: potassium 2: calcium 5; (iii) a molar ratio of citrate 3-4.5: calcium 4-6: potassium 2-3: and sodium 0-1.

The invention is further directed to a method for producing a dried calcium-rich composition comprising:
(i) mixing at least one source of citrate with at least one source of calcium and at least one metal source selected from:
a) an alkaline earth metal source; and
b) an alkali metal source;
in a molar ratio of at least three moles citrate, at least five moles of calcium and at least two moles of the at least one metal source so as to produce an organic calcium solution; and
(ii) drying the organic calcium solution so as to produce the dried calcium-rich composition, wherein said composition comprises at least 66% citrate on a dry weight basis, and wherein said composition comprises at least 15% calcium on a dry weight basis.

The invention is further directed to foods or nutritional product comprising the calcium enriched composition. The nutritional product may be a beverage or beverage concentrate comprising the calcium enriched composition. In particular, the beverages are milk based beverages that may be fortified with proteins, vitamins, minerals or their mixtures. Non-limiting examples of beverages are selected from soy milk, cow milk, camel milk, goat milk, or their mixtures. Such beverages may further comprise additional edible supplements selected from cocoa, vanilla, fruit or vegetable concentrates or flavorings.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

The present invention is thus directed to calcium comprising compositions, which are stable in food and beverages and in food and beverage supplements. Preferably the compositions are suitable for use in milk, soy milk and other "milk-like", "milk-containing", protein containing beverages or their mixtures. Despite the large number of supplements currently available and known in the art, many of them are unstable and precipitate out of solution over time. The products of the present invention may be used to meet the demand in the market for stable sources of calcium, which are suitable for adding to foods and beverages. The products of the present invention are used as supplements and do not affect the organoleptic properties or the taste of the food or beverage to which they are added. The calcium products of the present invention are both stable and do not typically precipitate during the storage of the food/beverage even after storage periods of about 70-80 days.

The present invention relates in particular to stable dried compositions of organic calcium, in the form of calcium citrate with at least one other additional metal, to methods for the preparation of these compositions and their use as calcium supplements. The products of this invention may be used either directly for enhancing uptake of calcium or as an additive in various food and beverages to fortify these food products with calcium. The compositions are stable in beverages and in food, to which they added.

The compositions of the present invention exhibit high bioavailability. The compositions of the present invention are stable in sterilization and pasteurization processes known in the art of food and beverage processing. The composition of the present invention does not require the co-addition of hydrocolloids in order to retain the calcium in a stable suspension.

Figure 1:
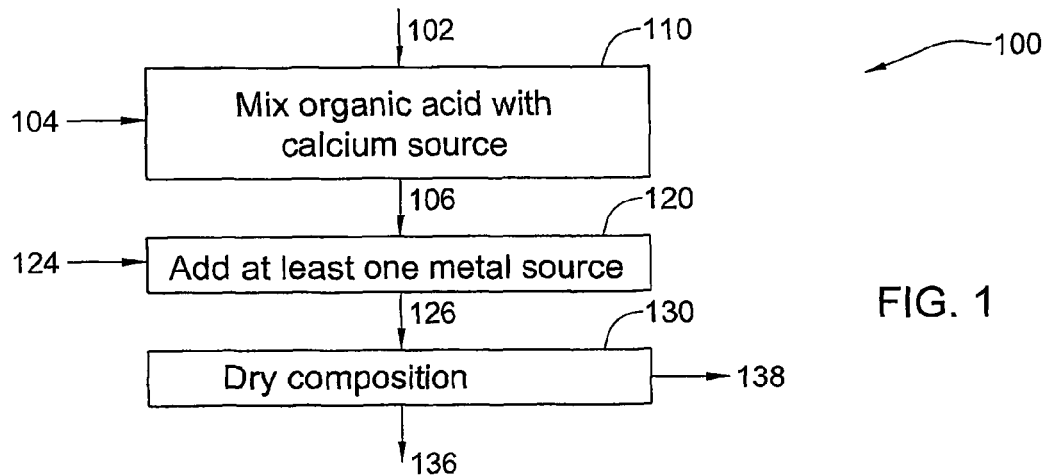
FIG. 1 is a simplified flowchart illustrating a process for producing a dried calcium-rich composition according to a preferred embodiment of the present invention.

Reference is now made to FIG. 1, which is a simplified flowchart 100 illustrating a process for producing a dried calcium-rich composition according to a preferred embodiment of the present invention.

In a first mixing step 110, an organic acid solution 102, being a citrate solution is mixed with a calcium source 104. The citrate solution which is citric acid or its salts, is typically in a concentration range of 0.1 to 0.5 M. Non limiting sources of calcium according to the present invention are selected from the group of calcium hydroxide, calcium oxide, calcium carbonate, calcium propionate, calcium gluconate, calcium citrate, calcium stearate, calcium fumarate, calcium glycerophosphate. The calcium source 104 is provided to produce a solution with molar ratio of Calcium to Citrate typically in the range of 1.1-1.3. Typically this step is performed in a standard mixed vessel well known in the art. This mixing step 110 typically takes up to 30 minutes. In this step 110, the vessel is typically cooled to a set temperature below 25° C. Cooling jackets known in the art, may be employed on a large scale, or the vessel may be at least partially immersed in a water bath on the small scale, as is known in the art. In the present invention different chillers were used (such as CH10TR nameplate number 30089, Unique, Nehalim, Israel or CC230, Huber High Precision Thermoregulation, Offenburg, Germany)

Typically, the citrate solution 102 is obtained commercially. Alternatively, it may be prepared in situ as is exemplified in FIG. 2 herein below.

Typically, solution 106 comprises 4 to 25% total dissolved solids (TDS). In some embodiments, there are 5 to 10% TDS in solution.

Solution 106 and/or solution 126 (described hereinbelow) typically has a pH value in the range of 4.5 to 12, and more preferably from 5 to 10.

In an addition step 120, at least one metal source 124 selected from an alkaline earth metal source and an alkali metal source is added to calcium citrate solution 106 to form a calcium metal citrate solution 126. This may be performed in the same or different vessel to that of step 110. The at least one metal source is selected from at least one potassium source, at least one magnesium source, at least one sodium source or their mixtures. Non-limiting examples of the potassium source are potassium hydroxide, potassium citrate, potassium carbonate and potassium bicarbonate. Typically the potassium salt is added in to produce the molar ratio of potassium to citrate in a range 0.6-0.8. Non-limiting examples of the magnesium source are magnesium oxide, magnesium hydroxide magnesium citrate, magnesium carbonate. Typically the magnesium salt is added in suitable concentration to produce the molar ratio of Magnesium and Citrate in range 0.1 to 0.25.

In the drying step 130, solution 126 is dried and liquid 138 is removed there from to form a dry calcium metal citrate composition 136. Step 130 typically drying solution 126 into a powder using a spray drying or freeze drying process in a dryer APV PSD52 (APV Nordic Anhydro, Silkeborg, Denmark) using the inlet air with temperature from 190 up to 350° C. as is known in the art. Excess liquid 138 is removed from the solution until a solid phase forms. The solid phase may be in the form of a powder, flakes, granules or other solid form.

The resultant composition 136 may then be suitably stored and/or packaged (not shown). The resultant composition typically has a bulk density of less than 0.6 g/cm$^3$, more typically, less than 0.5 g/cm$^3$.

Dry calcium metal citrate composition 136 typically has a composition as is shown in Table 1. It should be noted that all the examples herein of the composition produced comprises 7-10% adsorbed (crystalline) water.

TABLE 1

Typical Composition of a Calcium Metal Citrate Composition on a Dry Weight Basis*

| COMPONENT | RELATIVE MOLAR RATIO | PERCENT OF DRY COMPOSITION [WT/WT %] |
|---|---|---|
| CITRATE | 1 | 63-75 |
| CALCIUM | 0.8-2 | 13-18 |
| POTASSIUM | 0.4-1 | 6-10 |
| MAGNESIUM | 0.03-0.3 | 0.5-1.5 |

Figure 2:
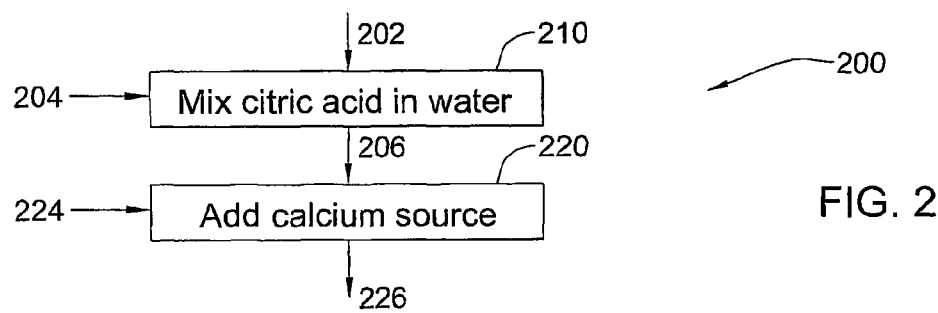
FIG. 2 is a simplified flowchart illustrating further details of one embodiment of step 110 of FIG. 1.

*it should be noted that the "dry weight" was calculated excluding up to 10% adsorbed water in the product Reference is now made to FIG. 2, which is a simplified flowchart 200 illustrating further details of one embodiment of step 110 of FIG. 1.

In a mixing step 210, water 202, such as deionized water, is mixed with a citrate containing solid or solution 204. Citrate containing solid or solution 204 is selected from citric acid (Sigma Aldrich Corporation, St. Louis, Mo., USA cat. Number C0759, C7129 or cat. Number C0706, C1909), sodium citrate (Sigma Aldrich Corporation, St. Louis, Mo., USA cat. Number C0759, C7129 or cat. Number S4641) and potassium citrate (Sigma Aldrich Corporation, St. Louis, Mo., USA cat. Number C0759, C7129 or cat. Number C8385). Typically suitable amount of citric acid or a citrate salt is added to provide a concentration of citrate ions in range up to 0.5 moles per liter of water. Water 202 and citrate containing solid or solution 204 are typically mixed at room temperature in any kind of well known in the art mixed vessel. This mixing step 210 typically takes up to 1 hour to provide a full dissolution. In this step 210, the vessel is typically cooled to a set temperature ranging from 5-25° C. Cooling jackets known in the art, may be employed on a large scale, or the vessel may be at least partially immersed in a water bath on the small scale, as is known in the art.

The resultant citrate solution 206, typically comprises 0.1-0.5 mol per liter of citrate.

In an addition step 220, a suitable source of calcium 224 is added to the citrate solution to form an organic calcium citrate solution 226. Typically this step is performed in a standard well known in the art mixed vessel. This step 220 typically takes up to 30 minutes while mixed. In this step 110, the vessel is typically cooled to a set temperature ranging below 25° C. Cooling jackets known in the art, may be employed on a large scale, or the vessel may be at least partially immersed in a water bath on the small scale, as is known in the art.

The calcium source may be selected from, but is not limited to, calcium citrate; calcium oxide, calcium hydroxide and calcium carbonate (of Sigma Aldrich Corporation, St. Louis, Mo., USA cat. Numbers C2178, C4830, C7887, or Fluka Buchs, Switzerland, cat. number 21118, cat. number 21120). The calcium source is provided to produce a molar ratio of calcium to citrate ion in range 1.1-1.3 in solution 226.

Figure 3:
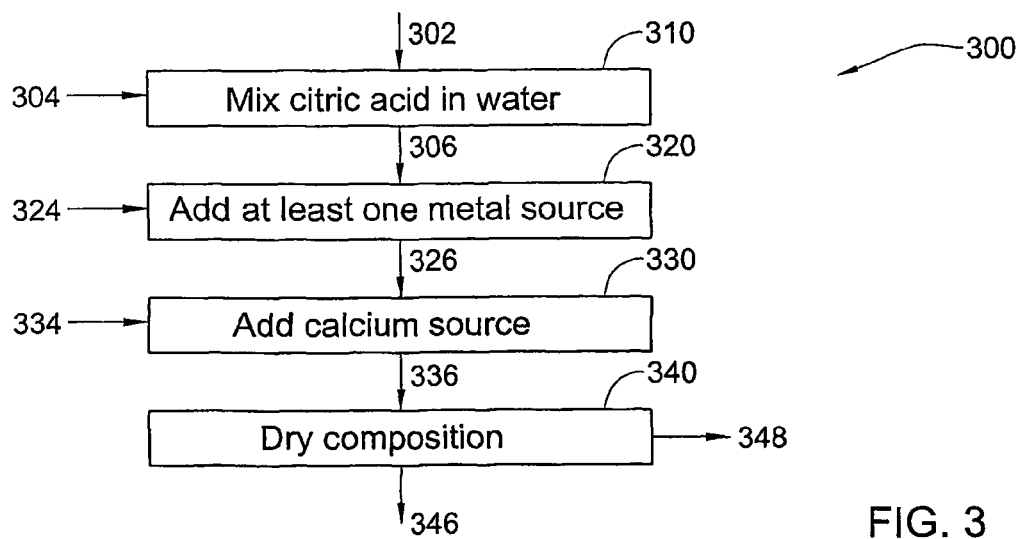
FIG. 3 is a simplified flowchart illustrating a process for producing a dried calcium-rich composition according to a preferred embodiment of the present invention.

Reference is now made to FIG. 3, which is a simplified flowchart 300 illustrating a process for producing a dried calcium-rich composition according to a preferred embodiment of the present invention.

In a mixing step 310, citric acid 304 (Gadot Biochemical Industries, Ltd., Haifa, Israel) is mixed in water 302, typically deionized water so as to produce a citric acid solution 306 of 0.1 to 0.5 moles per liter.

In a metal addition step 320, at least one source of metal 324 is added to the citric acid solution to form a metal rich citric acid solution 326. Typically, at least one source of potassium is added. The potassium source is selected from, but not limited to potassium hydroxide, potassium citrate, potassium carbonate and potassium bicarbonate (Sigma Aldrich Corporation, St. Louis, Mo., USA Cat. Numbers P9144, P5833, P4379, P6037, C8385, P5958, P1767, 60025, 60028). Typically the potassium salt is added in to produce the molar ratio of potassium to citrate in a range 0.6-0.8. In some embodiments, Sodium was used instead of potassium. In some embodiments, ammonium was used instead of potassium or sodium.

In some embodiments, the magnesium source is selected from, but not limited to, magnesium oxide, magnesium hydroxide, magnesium citrate, magnesium carbonate, (Sigma Aldrich Corporation, St. Louis, Mo., USA Cat. Numbers M7179, M5671, M5421, M8511, 30.77-2, M7861, and Merck & Co, Inc, Whitehouse Station, N.J., USA Cat. Numbers 105904)). Typically the magnesium salt is added in a suitable concentration to produce the molar ratio of magnesium and citrate in range 0.1 to 0.25. In some embodiments, no magnesium is added.

In some embodiments, step 330 is performed before step 320. Other variations on the flowcharts of FIGS. 1-3 also fall within the scope of the present invention.

In a second addition step 330, a calcium source 334 is added to solution 326 so as to form a calcium metal citrate solution 336.

The calcium source 334 may be selected from, but is not limited to, calcium citrate; calcium oxide, calcium hydroxide and calcium carbonate (Sigma Aldrich Corporation, St. Louis, Mo., USA cat. Numbers C2178, C4830, C7887, or Fluka Buchs, Switzerland, cat. number 21118, cat. number 21120). The calcium source is provided to produce solution 336 with molar ratio of Calcium to Citrate in range 1.1-1.3. The process conditions in this step and in step 330 may be similar to, identical to or different from those of step 120 of FIG. 1.

In a drying step 340, solution 336 is dried, liquid 348 is removed there from to form a dry calcium metal citrate composition 346. Step 340 typically dries solution 336 into a powder using a spray drying or freeze drying process in a dryer (APV PSD52, APV-Nordic Anhydro, Silkeborg, Denmark) using the inlet air with temperature from 190 up to 350 Degrees Celsius as is known in the art. Excess liquid 348 is removed from the solution until a solid phase forms. The solid phase may be in the form of a powder, flakes, granules or other solid form. The resultant composition 346 may then be suitably stored and/or packaged (not shown). Typically, the composition obtained has a bulk density of less than 0.5 g/cm$^3$.

Figure 4:
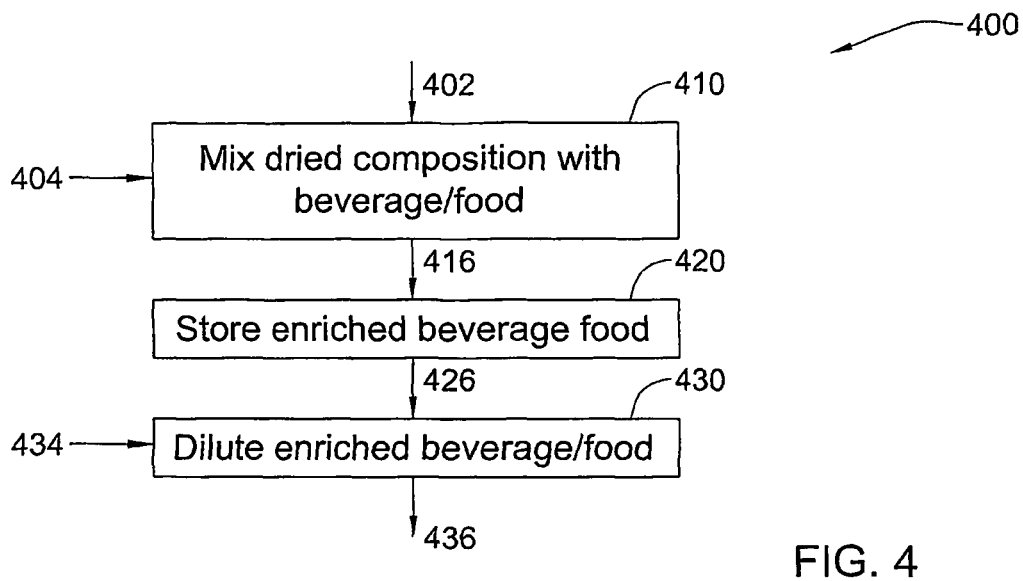
FIG. 4 is a simplified flowchart illustrating a process for supplementing a food or beverage with the dried calcium-rich composition according to a preferred embodiment of the present invention.

Reference is now made to FIG. 4, which is a simplified flowchart 400 illustrating a process for supplementing a food or beverage with the dried calcium-rich composition according to a preferred embodiment of the present invention.

In a mixing step 410, a dried calcium metal citrate composition 402 is mixed with a food or beverage 404 to form calcium enriched beverage/food 416. Composition 402 may be similar or identical to composition 136 or composition 346. The food may be in a liquid or solid state. The food may be exemplified by, but not limited to a cheese, yoghurt, cream, spread, cereal, or chocolate.

Non-limiting examples of beverages according to the present invention are fruit or vegetable based beverages, milk-based beverages, that may further comprise flavoring additives such as proteins, minerals or vitamins. Thus these may be milk, milkshake, nectars, or chocolate milk. The milk may be selected from, but not limited to, soy milk, reconstituted milk formula, goat milk, sheep milk, camel milk, substitute milk, cow milk and human milk or beverages based on them.

The ratio of composition 402 added to a liquid food/beverage 404 is typically suitable to provide a Calcium concentration up to 1.5 RDA of Calcium per liter. Calcium enriched beverage/food 416 typically comprises 1200 mg/l calcium.

Alternatively, calcium enriched beverage/food 404 is in a solid form and is mixed with composition 402 in any kind of well known in the art mixed vessels for about 15 minutes or till the homogeneous dispersion is obtained.

In an optional storage step 420, a liquid calcium enriched beverage/food 416 is stored for a period of few months at ambient conditions or during refrigeration. The properties of stored calcium enriched beverage/food 426 are compared to those of calcium enriched beverage/food 416. Typically, the composition is stable in the liquid and less than 10% of the calcium precipitates out of the liquid. In accordance with the stability of the added calcium fortifying composition, the initial calcium concentration introduced into the food/beverage 426 is maintained, where it preferably comprises at least 1200 mg/L of calcium.

In an optional dilution step 430, stored calcium enriched beverage/food 426 is diluted with water 434 to form a ready-to-use calcium enriched beverage/food product 436. For example, beverage/food 426 may be in a concentrated form such as a milk powder, baby milk liquid/solid formula, cream or concentrate, which may be diluted for use with water according to the relevant ratio or instructions provided therewith.

In some other embodiments, food product 404 is pre-dried and is reconstituted in step 430. Non-limiting examples are dried mashed potatoes, dried packet soups, milk powder, meat, yeast and protein extracts and "heat and eat" meals.

Figure 5:
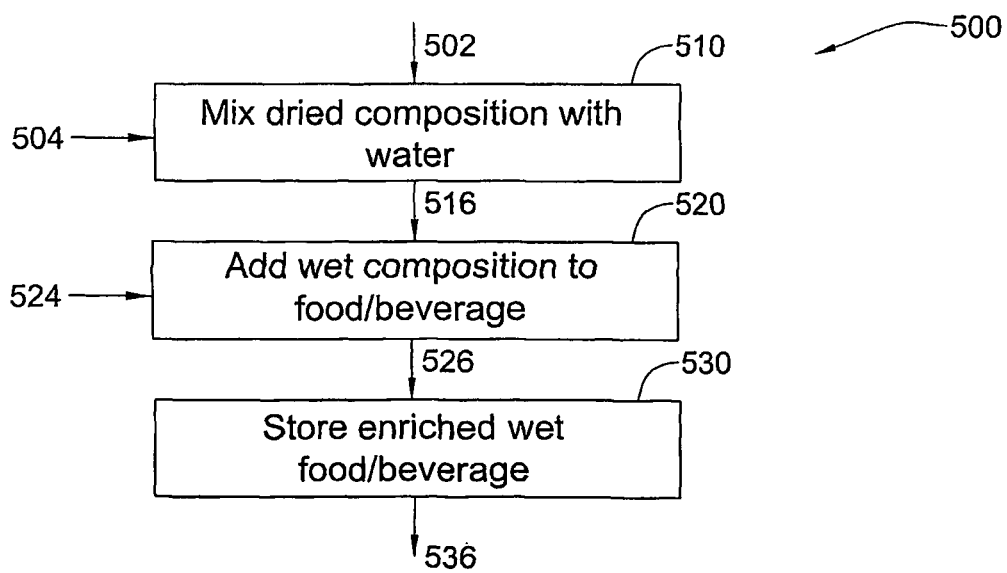
FIG. 5 is another simplified flowchart illustrating a process for supplementing a food or beverage with the dried calcium-rich composition according to a preferred embodiment of the present invention.

Reference is now made to FIG. 5, which is a simplified flowchart 500 illustrating a process for supplementing a food or beverage with the dried calcium-rich composition according to a preferred embodiment of the present invention.

In a mixing step 510, a dried calcium rich composition 502 is mixed with water 504 to form a wet calcium rich composition 516.

Composition 502 may be similar or identical to composition 136 or composition 346. Step 510 is performed in a any kind of well known in the art mixing vessel until an homogeneous suspension is obtained.

Typically about 100 g of composition 502 is added per liter of water such that the wet calcium rich composition comprises about 15 g calcium/l.

In an addition step 520, wet composition 516 is added to food/beverage 524 to form calcium-enriched food/beverage 526. The calcium-enriched food/beverage typically comprises 1200 mg calcium/l.

Step 520 is performed in any kind of well known in the art mixing for about 15 min or until the homogeneous suspension obtained.

In an optional storage step 530, calcium-enriched food/beverage 526 is stored for a period of at least a few month at ambient conditions or at refrigeration. The properties of stored calcium enriched beverage/food 536 are compared to those of calcium enriched beverage/food 526. Typically, less than 10% of the calcium precipitates out of the liquid. In some embodiments less than 5% of the calcium precipitates out of the liquid such that stored beverage/food 536 comprises at least 1200 mg/l calcium.

Example 1

1840 ml of deionized water were placed in a 5 L beaker and the temperature kept in the range of 5-25° C. While stirring, 66.5 g citric acid was added followed by 2.5 g of MgO. Thereafter, 23.3 gr CaO were added. Finally, 13 g KOH was added. The mixture was well stirred, dried (as described with reference to the flowcharts hereinabove). The dry product obtained had properties in the range of those described in Table 1 hereinabove.

Example 2

920 ml of deionized water were placed in a 5 L beaker and the temperature kept in the range of 5-25° C. While stirring, 36.5 g citric acid was added followed by 13.6 g of CaO. Finally, 6.5 g KOH were added. The mixture was well stirred and dried (as described with reference to the flowcharts hereinabove). The dry product obtained had properties in the range of those described in Table 1 hereinabove.

Example 3

920 ml of deionized water were placed in a 5 L beaker and the temperature kept in the range of 5-25° C. While stirring, 66.5 g citric acid was added followed by 2.5 g of MgO. Thereafter were added 23.3 gr CaO. Finally, there were added 13 gr KOH. The mixture was well stirred, dried (as described with reference to the flowcharts hereinabove). The dry product obtained had properties in the range of those described in Table 1 hereinabove.

Example 4

To 1000 ml of cow milk 3% fat (Tnuva, Rehovot, Israel), 6.7 grams of composition, prepared as described in Example 1, was added while stirring with well known in the art laboratory magnetic stirrer. The initial concentration of calcium was tested and found 2230 mg/liter. After storing for 6 days at 4 Degrees Celsius, the concentration of Calcium in the upper layer was tested again and found to be 2225 mg/liter.

Example 5

To 1000 ml of natural soy milk (Alpro N.V., Wevelgem, Belgium), 6.7 g of composition (prepared as described in example 1) was added while stirred with a laboratory magnetic stirrer to form an enriched soy milk. The initial concentration of calcium in the enriched soy milk was tested and found 1327 mg/liter. After storing for 6 days at 4 Degrees Celsius, the concentration of calcium of the enriched soy milk was tested again and found 1325 mg/liter Example 6

1840 ml of deionized water were placed in a 5 L beaker and the temperature kept in the range of 5-25° C. While stirring, 66.5 g citric acid were added followed by 2.5 g of MgO. Thereafter were added 23.3 gr CaO. Finally, there were added 7.7 gr NaOH. The mixture was well stirred, dried (as described with reference to the flowcharts hereinabove).

Example 7

To 1000 ml of natural soy milk (Alpro N.V., Wevelgem, Belgium) 6.7 g of composition (prepared as described in Example 6 hereinabove) was added under stirring with a laboratory magnetic stirrer so as to form enriched soy milk. The initial concentration of calcium was tested in the enriched soy milk and found to be 1305 mg/liter. After storing for 6 days at 4 Degrees Celsius, the concentration of Calcium in the enriched soy milk was tested again and found to be 1306 mg/liter

Example 8

To 1000 ml of natural soy milk (Alpro N.V., Wevelgem, Belgium), 6.7 g of composition (prepared as described in Example 1 hereinabove) was added under stirring with a laboratory magnetic stirrer to form enriched soy milk. In addition, 0.2 g of Cappa Karragenan (Sigma Aldrich Corporation, St. Louis, Mo., USA cat. Number C1263) was added. The initial concentration of calcium in the enriched soy milk was tested and found to be 1396.7 mg/liter. After storing for 6 days at 4 Degrees Celsius, the concentration of calcium in the enriched soy milk was tested again and found 1401.1 mg/liter

Example 9

To 1000 ml of natural soy milk (Alpro N.V., Wevelgem, Belgium) 6.7 g of composition (prepared as described in Example 1 hereinabove) was added while stirred with a laboratory magnetic stirrer to form enriched soy milk. The enriched soy milk was passed through homogenizer (APV PSD52, APV Nordic Anhydro, Silkeborg, Denmark). Thereafter, the initial concentration of calcium was tested and found 1446.6 mg/liter. After storing for 6 days at 4 Degrees Celsius, the concentration of calcium of the enriched soy milk was tested again and found 1432.3 mg/liter

Example 10

The material was prepared as described in Example 1 hereinabove, but the aqueous suspension was stored for 10 hours prior to the drying step. Thereafter, the material was dried as described with reference to the flowcharts hereinabove. The dry product obtained had properties in the range of those described in Table 1 hereinabove.

Example 11

To 1000 ml of natural soy milk (Alpro N.V., Wevelgem, Belgium) 6.7 g of composition (prepared as described in Example 10) was added under stirring with a the art laboratory magnetic stirrer and an enriched soy milk product was formed. The initial concentration of calcium in the product was tested and found 1267 mg/liter. After storing for six days at 4 Degrees Celsius, the concentration of calcium in the product was tested again and found 1266 mg/liter

Example 12

To 1000 ml of natural soy milk (Alpro N.V., Wevelgem, Belgium) 6.7 g of composition (prepared as described in Example 1 hereinabove) was added under stirring employing a laboratory magnetic stirrer to form a calcium-enriched composition. The calcium-enriched composition underwent ultra-high temperature (UHT) treatment (4 sec at 140° C.) as is known in the art. The initial concentration of calcium in the calcium-enriched composition was tested and found 905 mg/liter. After storing for 7 days at 4 Degrees Celsius, the concentration of calcium in the calcium-enriched composition was tested again and found 906 mg/liter. After storing for another 7 days at 4 Degrees Celsius, the concentration of calcium in the calcium-enriched composition was tested again and found 905.5 mg/liter. After retention of 70 days at 4 Degrees Celsius, the concentration of calcium in the calcium-enriched composition was tested again and found 905 mg/liter.

Example 13

1840 ml of deionized water were placed in a 5 L beaker and the temperature kept in the range of 5-25° C. While stirring, 66.5 g citric acid were added followed by 2.5 g of MgO. Thereafter were added 23.3 g CaO. Finally, there were added 8.12 gr $NH_4OH$. The mixture was well stirred and dried (as described with reference to the flowcharts hereinabove). The dry product obtained had properties in the range of those described in Table 1 hereinabove.

Example 14

To 1000 ml of natural soy milk (Alpro N.V., Wevelgem, Belgium) 6.7 g of composition (prepared as described in Example 13) was added under stirring, employing a laboratory magnetic stirrer, to form enriched soy milk. The initial concentration of calcium in the enriched soy milk was tested and found 1332 mg/liter. After storing for 6 days at 4 Degrees Celsius, the concentration of calcium in the enriched soy milk was tested again and found 1343 mg/liter.

Example 15

To 1000 ml of milk based cocoa beverage (Machlevot Yutveta, Israel) 2 g of composition (prepared as described in Example 1) was added under stirring, employing a laboratory magnetic stirrer, to form Calcium enriched beverage. The initial concentration of calcium in the enriched beverage was tested and found 1402 mg/liter. After storing for 6 days at 4 Degrees Celsius, the concentration of calcium in the enriched beverage was tested again and found 1390 mg/liter.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art.

The invention claimed is:
1. A calcium rich composition, comprising:
    at least one source of calcium, the calcium being present in an amount of at least 15% (wt/wt) on a dry weight basis;
    at least one source of magnesium;
    at least one metal source selected from the group consisting of an alkaline earth metal source other than calcium and an alkali metal source; and
    at least one source of citrate, the citrate being present in an amount of at least 66% (wt/wt) on a dry weight basis;
    wherein the composition has a bulk density of less than 0.5 $g/cm^3$.
2. The composition according to claim 1, wherein the calcium is present in an amount of from 15% to 20% (wt/wt) and the citrate is present in an amount of at least 71% (wt/wt) citrate on a dry weight basis.

3. The composition according to claim 1, wherein the calcium source is selected from the group consisting of calcium hydroxide, calcium oxide, calcium carbonate, calcium propionate, calcium gluconate, calcium citrate, calcium stearate, calcium fumarate and calcium glycerophosphate.

4. The composition according to claim 1, wherein the citrate source is selected from the group consisting of citric acid, citric acid monohydrate, citric acid mono-, di- or tri-sodium salt, citric acid tripotassium salt and ammonium citrate.

5. The composition according to claim 1, wherein the at least one metal source is selected from the group consisting of a source of sodium, a source of potassium, and mixture thereof.

6. The composition according to claim 1, wherein the source of potassium is selected from the group consisting of potassium hydroxide, potassium citrate, potassium carbonate and potassium bicarbonate, wherein the source of magnesium is selected from the group consisting of magnesium oxide, magnesium hydroxide, magnesium carbonate and magnesium citrate, and wherein the source of sodium is selected from the group consisting of sodium hydroxide, sodium citrate, sodium carbonate and sodium bicarbonate.

7. The composition according to claim 1, wherein the composition has a molar ratio of 3-4.5 citrate: 4-6 calcium: 2-3 of the at least one metal and magnesium.

8. The composition according to claim 7, wherein the composition has a molar ratio of citrate 3-4.5: calcium 4-6: potassium or sodium 2-3: sodium and magnesium 0.1-1.

9. The composition according to claim 7, wherein the composition has a molar ratio of citrate 4: potassium 2: calcium 5.

10. The composition according to claim 1, further comprising stabilizers, coloring agents or emulsifiers.

11. The composition according to claim 1, wherein the composition exists in a dry form selected from the group consisting of powder, granules and flakes.

12. The composition according to claim 1 dissolved or suspended in an aqueous based solution.

13. A food or nutritional product, comprising:
the composition according to claim 1.

14. The food or nutritional product according to claim 13, wherein the food or nutritional product is a beverage.

15. The food or nutritional product according to claim 13, wherein the food or nutritional product is a beverage comprising one or more foodstuffs selected from the group consisting of a whole fruit, any portion of a whole fruit; a whole vegetable, any portion of a whole vegetable, and milk.

16. The food or nutritional product according to claim 15, wherein the beverage is a milk based beverage selected from the group consisting of soy milk, reconstituted milk formula, goat milk, sheep milk, camel milk, substitute milk, cow milk, oat milk, human milk and mixtures thereof.

17. The food or nutritional product according to claim 14, wherein the beverage comprises one or more ingredients selected from the group consisting of flavorings, vitamins, minerals and proteins.

18. The food or nutritional product according to claim 14, wherein the food or nutritional product is a beverage, and the composition is present in an amount of at least 5 gr/L.

19. The food or nutritional product according to claim 14, wherein the food or nutritional product is a beverage that is storage stable for a period of at least 70 days.

20. A method for producing a dried calcium-rich composition, comprising:
mixing at least one source of citrate with at least one source of calcium, at least one source of magnesium, and at least one metal source selected from the group consisting of an alkaline earth metal source other than calcium and an alkali metal source, in a molar ratio of at least three moles of citrate to at least five moles of calcium to at least two moles of magnesium and the at least one metal, so as to produce an organic calcium solution; and
drying the organic calcium solution so as to produce the dried calcium-rich composition,
wherein the composition comprises at least 66% citrate on a dry weight basis and at least 15% calcium on a dry weight basis.

21. A calcium rich composition, comprising:
at least one source of calcium, the calcium being present in an amount of at least 15% (wt/wt) on a dry weight basis;
at least one source of magnesium;
at least one source of metal selected from the group consisting of an alkaline earth metal source other than calcium and an alkali metal source; and
at least one source of citrate, the citrate being present in an amount of at least 66% (wt/wt) on a dry weight basis;
wherein the composition has a bulk density of less than 0.5 g/cm$^3$, and the composition is stable upon dissolving in a liquid.

* * * * *